(12) United States Patent
Suzuki et al.

(10) Patent No.: US 6,375,988 B1
(45) Date of Patent: Apr. 23, 2002

(54) DRUG COMPOSITION WITH CONTROLLED DRUG RELEASE RATE

(75) Inventors: Makoto Suzuki, Sakura; Kenji Ishigaki, Chiba; Minoru Okada, Inzai; Kenji Ono, Sakura; Shuichi Kasai, Narita; Katsumi Imamori, Yotsukaido, all of (JP)

(73) Assignee: SSP Co., Ltd., Tokyo (JP)

( * ) Notice: Subject to any disclaimer, the term of this patent is extended or adjusted under 35 U.S.C. 154(b) by 0 days.

(21) Appl. No.: 09/172,270

(22) Filed: Oct. 14, 1998

(30) Foreign Application Priority Data

Oct. 27, 1997 (JP) .............................. 9-294008

(51) Int. Cl.$^7$ ................................ A61K 9/50
(52) U.S. Cl. ........................ 424/499; 514/952; 424/488; 424/436
(58) Field of Search ................ 424/484, 499, 424/488, 422, 436; 514/777, 773–76, 952, 966

(56) References Cited

U.S. PATENT DOCUMENTS

| | | | |
|---|---|---|---|
| 4,814,176 A | * | 3/1989 | Makino et al. |
| 5,061,492 A | | 10/1991 | Hiroaki et al. |
| 5,116,824 A | * | 5/1992 | Miyata et al. |
| 5,416,071 A | * | 5/1995 | Igari et al. |
| 5,629,011 A | * | 5/1997 | Illum et al. |
| 5,885,609 A | * | 3/1999 | Amiji et al. |

FOREIGN PATENT DOCUMENTS

| | | |
|---|---|---|
| EP | 0 562 864 | 9/1993 |
| WO | WO 95/13055 | 5/1985 |
| WO | WO 91/17744 | 11/1991 |
| WO | WO 92/20716 | 11/1992 |
| WO | WO 93/08818 | 5/1993 |
| WO | WO 93/11805 | 6/1993 |
| WO | WO 93/21906 | 11/1993 |
| WO | WO 96/03973 | 2/1996 |

OTHER PUBLICATIONS

Chemical Abstracts, vol. 114, No. 10, Mar. 11, 1991, AN 88722t, CS 264,719, Dec. 15, 1989.
Derwent Abstracts, AN 95–110565, JP 07–033682, Feb. 3, 1995.
Derwent Abstracts, AN 94–156569, JP 06–100468, Apr. 12, 1994.

* cited by examiner

*Primary Examiner*—Edward J. Webman
(74) *Attorney, Agent, or Firm*—Oblon, Spivak, McClelland, Maier & Neustadt, P.C.

(57) ABSTRACT

This invention relates to a drug composition with a controlled drug release rate. The drug composition comprises:
  a matrix formed of the following ingredients (a) and (b):
   (a) a biodegradable, biocompatible high-molecular substance and/or polyvalent metal ions or polyvalent metal ion source, and
   (b) hyaluronic acid or a salt thereof; and
  a drug incorporated as an ingredient (c) in said matrix. The drug composition has biodegradability and biocompatibility, permits easy control of a release rate of the drug, and can persistently exhibit its pharmacological effect over a long time.

13 Claims, 5 Drawing Sheets

DRUG COMPOSITION WITH CONTROLLED DRUG RELEASE RATE

TECHNICAL FIELD

This invention relates to a drug composition with a controlled drug release rate, which makes use of a particular matrix as a carrier.

BACKGROUND ART

From the standpoint of exhibition of drug efficacy and a reduction in side effects, it is preferred for a drug to remain at a target site only for the length of time and in the quantity necessary. Research is therefore under way on systems whereby certain specific substances are used as carriers for drugs, the drugs being released only in the quantity and for the length of time necessary.

For example, hyaluronic acid is a polysaccharide which is found in the living body. It has been studied for its physiological activities and also as a carrier for other drugs. Conventionally-known examples of drug release systems ma king use of hyaluronic acid as a carrier can include one containing a physiologically-active peptide in an aqueous solution of hyaluronic acid (JP kokai 2-213), those making use of hyaluronic acid crosslinked with an epoxy compound, divinyl sulfone, a carbodiimide or the like (JP kokai 61-138601, JP kokai 60-233101, JP kokai 5-140201, and JP kokai 7-102002), a sustained release composition of hyaluronic acid and alginic acid (JP kokai 6-100468), a polyion complex of hyaluronic acid and a cationic polyacrylic acid derivative (JP kokai 7-33682), and one making use of a hyaluronic acid derivative (JP kokai 5-255124).

However, the techniques of JP kokai 2-213 and JP kokai 6-100468 have a problem in that they are not sufficiently effective in controlling a drug release rate. The techniques of JP kokai 61-138601, JP kokai 60-233101, JP kokai 5-140201 and JP kokai 7-102002 are accompanied by a problem in that the crosslinking materials have low compatibility with the living body and have no biodegradability. The technique of JP kokai 7-33682 involves a problem in that the cationic polyacrylic acid derivative does not have biodegradability. Further, the technique of JP kokai 5-255124 has problems in that substantial time is required for preparation into a unit dosage form and the release rate of a drug is hardly controllable.

An object of the present invention is to provide a drug composition which has biodegradability and biocompatibility, permits easy control of a drug release rate, and can persistently exhibit its pharmacological effect over a long time.

DISCLOSURE OF THE INVENTION

With a view to achieving the above-described object, the present inventors have therefore proceeded with extensive research. As a result, it has been found that a drug composition with a drug incorporated in a matrix, which has been formed from a biodegradable, biocompatible high molecular substance and/or polyvalent metal ions or polyvalent metal ion source and hyaluronic acid, has biocompatibility and biodegradability and permits free control of the release rate of the drug, leading to the completion of the present invention.

The present invention therefore provides a drug composition with a controlled drug release rate, which comprises:
a matrix formed of the following ingredients (a) and (b):
  (a) a biodegradable, biocompatible high-molecular substance and/or polyvalent metal ions or polyvalent metal ion source, and
  (b) hyaluronic acid or a salt thereof; and
a drug incorporated as an ingredient (c) in said matrix.

BEST MODE FOR CARRYING OUT THE INVENTION

Figure 1:
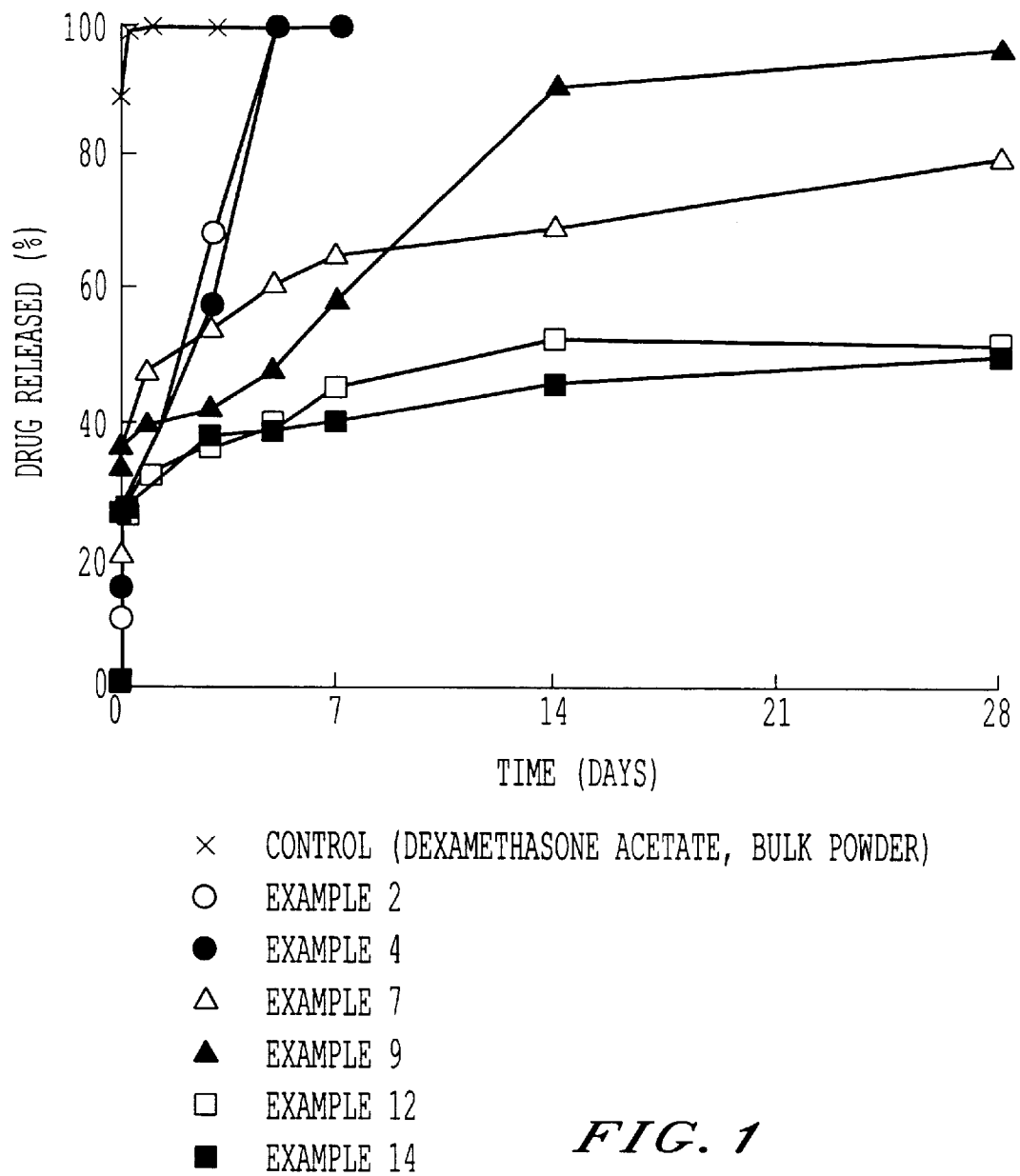
FIG. 1 is a graph showing release profiles of dexamethasone from drug compositions, which had been prepared using substances of different kinds, contained dexamethasone acetate and also contained hyaluronic acid as a carrier, into water.

In the drug composition according to the present invention, the high-molecular substance having biodegradability and biocompatibility and/or polyvalent metal ions (ingredient (a)) is used. They can be degraded and absorbed in the living body without deleterious effects. Illustrative of the high-molecular substance are polypeptides, polyamino acids, and cationic polysaccharides. Preferably usable examples can include gelatin, sodium casein, albumin and lysozyme chloride, as polypeptides; poly-L-lysine as a polyamino acid; chitosan as a cationic polysaccharide; and $Ca^{2+}$, $Al^{3+}$ and $Fe^{3+}$ as polyvalent metal ions. No particular limitation is imposed on the polyvalent metal ion source, insofar as it can be ionized substantially when formed into a desired solution. Among such sources, $CaCl_2$, $AlCl_3$ and $FeCl_3$ are preferred. Further, chitosan having an acetylation degree of from 30 to 100% may be used preferably, although no particular limitation is imposed on the type of chitosan. They can be used either singly on in combination. The release of a drug from a drug composition can be controlled at will by selecting one or more of such substances and metal ions as needed.

The content of the ingredient (a) in the drug composition according to the present invention may range preferably from 5 to 75 wt. %, notably from 10 to 50 wt. %. The content range of from 5 to 75 wt. % makes it possible to easily control the release rate of the drug.

The viscosity average molecular weight of hyaluronic acid or a salt thereof (ingredient (b)) may be preferably from 600,000 to 2,000,000, especially from 1,000,000 to 2,000,000. The range of from 600,000 to 2,000,000 makes it possible to easily control the release rate of the drug. The content of hyaluronic acid or the salt thereof in the drug composition according to the present invention may range preferably from 5 to 95 wt. %, notably from 10 to 90 wt. %. The content range of from 5 to 95 wt. % makes it possible to easily control the release rate of the drug.

In the present invention, the ingredients (a) and (b) make up the matrix. The term "matrix" as used herein means a base material which can control the release rate of a drug contained therein.

Usable examples of the drug (ingredient (c)) incorporated in the drug composition according to the present invention can include anti-inflammatory drugs, antiepileptics, hypnotic sedatives, antipyretic analgesics, stimulants, antihypnotics, drugs for vertigo, drugs for the central nervous system, skeletal muscle relaxants, drugs for the autonomic nervous system, autonomic ganglionic blockers, drugs for the peripheral nervous system, opthalmic drugs, drugs for sense-organs, cardiacs, antiarrhythmics, diuretics, anti-hypertensives, vasoreinforcements, vasoconstrictors, vasodilators, antiarteriosclerotics, circulatory drugs, respiratory stimulants, antitussive expectorants, drugs for respiratory organs, peptic ulcer drugs, stomachic digestants, antacids, cathartics, cholagogues, digestive drugs, hormonal agents, urinary tract disinfectants, uterotonics, urogenital drugs, drugs for anus diseases, vitamins, nutritive roborants, drugs for blood or body fluid, drugs for hepatic diseases, antidotes, habitual intoxication drugs, antipodagrics, enzyme preparations, antidiabetics, cell activation drugs, antitumor agents, antibiotics, chemotherapeutic agents, and arthritis therapeutics. They can be used either singly or in combination. When it is desired to use hyaluronic acid or a salt thereof as a drug, hyaluronic acid or the salt thereof is already contained as the ingredient (b) so that no additional hyaluronic acid or the salt thereof is required as the ingredient (c). In this case, hyaluronic acid or the salt thereof forms a matrix with the ingredient (a), and release of hyaluronic acid supported in the matrix is controlled. When hyaluronic acid or a salt thereof is added as the ingredient (b), the proportion of hyaluronic acid may range preferably from 50 to 90 wt. %, especially from 80 to 90 wt. %.

The content of such a drug in the drug composition according to the present invention may preferably be not higher than 90 wt. %, and more preferably, may range from 0.1 to 90 wt. %, with a range of from 0.1 to 50 wt. % being particularly preferred. A drug content not higher than 90 wt. % makes it possible to easily control the release rate of the drug.

No particular limitation is imposed on the form of the drug composition according to the present invention. For example, it can be formed into a solid, a semi-solid, pellets, a fine powder, microcapsules or the like. Of these, microcapsules are particularly preferred. Microcapsules permit easy preparation into a unit dosage form upon administration to the human body. When formed into microcapsules, the average particle size may range preferably from 30 to 500 $\mu$m, especially from 30 to 150 $\mu$m. The particle size range of from 30 to 500 $\mu$m makes it possible to easily control the release rate of the drug. Incidentally, the term "microcapsules" as used herein means minute receptacles made of the matrix and containing the drug distributed in the matrix as a carrier.

No particular limitation is imposed on the unit dosage form of the drug composition according to the present invention. It can be used, for example, as an injection, oral preparation, external preparation, suppositories, eye drop, implant or the like. Use in the form of an injection is particularly preferred. When employed as an injection, it can be used as a water-base, suspended injection which may contain a suspending agent, a stabilizer, a buffer, a preservative, a thickening agent, an isotonicity and/or the like as needed. Although no particular limitation is imposed on the administration site, subcutaneous, intramuscular, intraperitoneal, intra-articular or like administration is preferred. When employed as an oral preparation, the drug composition can be formed into tablets, granules, a powder or the like. When used as an external preparation, the drug composition can be formed into an ointment, a cream or the like.

In the present invention, excipients, stabilizers, preservatives, surfactants, buffers and the like, which are commonly employed in drug compositions, can be contained to extents not impairing the effects of the present invention.

The drug composition according to the present invention can be prepared, for example, by submerged hardening which will be described hereinafter. Namely, a solution of the ingredient (b) is added under stirring to a solution of the ingredient (a), followed by the addition of the ingredient (c). The resulting mixture is stirred until a solid matter is formed. The solid matter is collected by filtration and is then washed, dried and ground, whereby the drug composition can be obtained. Upon preparation of the drug composition, the ingredient (c) may be dissolved or dispersed beforehand in the solution of the ingredient (b). The solution of the ingredient (b) may be in the form of a gel. In this case, the resulting product will be in a semi-solid form. This semi-solid product can be molded or otherwise formed into a drug composition.

The above-described solid matter may preferably be in such a form as containing the ingredient (c) uniformly dispersed in a matrix obtained by intimately mixing the solution of the ingredient (b) and the solution of the ingredient (a), so that the release rate of the drug can be easily controlled. It is therefore preferred to sufficiently continue stirring during the formation of the solid matter.

Further, the solution of the ingredient (a) may preferably an aqueous solution or an acetic acid solution. An aqueous solution is preferred especially when a $Ca^{2+}$, $Al^{3+}$ or $Fe^{3+}$ source or lysozyme chloride is used as the ingredient (a). However, an acetic acid solution is preferred especially when gelatin, sodium casein, albumin, lysozyme chloride, poly-L-lysine or chitosan is employed as the ingredient (a). This makes it possible to facilitate the dissolution of the ingredient (a). In the solution of the ingredient (a), the content of the ingredient (a) may range preferably from 0.1 to 50 wt. %. The content range of from 0.1 to 50 wt. % makes it possible to easily control the release rate of the drug from the drug composition. A high concentration is preferred especially when polyvalent metal ions or a polyvalent metal ion source is used, while a low concentration is preferred when a polypeptide, polyamino acid or cationic polysaccharide is employed.

The solution of the ingredient (b) may preferably be an aqueous solution. In the solution of the ingredient (b), the concentration of the ingredient (b) may preferably be 3.0 wt. % or lower, with 0.5 to 1.5 wt. % being particularly preferred. This concentration range makes it possible not only to readily prepare the drug composition but also to easily control the release rate of the drug.

To prepare the drug composition of the present invention into microcapsules, the preparation can be conducted by submerged dropping hardening, submerged hardening making use of emulsification, or a like method. According to submerged dropping hardening, micro-capsules are formed, for example, by dropping small droplets of the solution of the ingredient (b) into the solution of the ingredient (a) and then allowing the small droplets there. According to submerged hardening making use of emulsification, the solution of the ingredient (b) is added to a hydrophobic solvent and is then emulsified there. The thus-formed emulsion is added under stirring to the solution of the ingredient (a). After the resulting mixture is stirred at room temperature, microcapsules are allowed to occur. The microcapsules are collected by filtration, washed and then dried, whereby microcapsules are obtained as the drug composition. In this case, the ingredient (c) may generally be added beforehand in the solution of the ingredient (a) and/or the solution of the ingredient (b) unless addition of the ingredient (c) in a different manner is required for its physical and/or chemical properties.

The present invention will next be described in further detail by the following examples. It should however be borne in mind that the present invention shall not be limited to or by the following examples.

EXAMPLE 1

Dexamethasone sodium phosphate (100 mg) and sodium hyaluronate (700 mg) were dissolved in purified water (68.6 g). The resulting solution was added gradually under stirring at 1,000 rpm into a 50% (W/W) aqueous calcium chloride solution (70 g). After the thus-obtained mixture was stirred for 60 minutes, a solid matter was allowed to occur. The solid matter was collected by filtration, washed with ethanol, dried and then ground, whereby a drug composition (the content of dexamethasone sodium phosphate: 3.2%) was obtained.

EXAMPLES 2–6

In each example, dexamethasone acetate and sodium hyaluronate in amounts shown in Table 1 were dissolved in purified water. The resulting solution was added gradually under stirring at 1,000 rpm into a 50% (W/W) aqueous calcium chloride solution (25 g). After the thus-obtained mixture was stirred for 60 minutes, a solid matter was allowed to occur. The solid matter was collected by filtration, washed with ethanol, dried and then ground, whereby a drug composition having the drug content indicated in Table 1 was obtained.

TABLE 1

| | Dexamethasone acetate (mg) | Sodium hyaluronate (mg) | Drug content (%) |
|---|---|---|---|
| Example 2 | 50 | 225 | 11.9 |
| Example 3 | 100 | 200 | 19.0 |
| Example 4 | 200 | 150 | 42.4 |
| Example 5 | 300 | 100 | 63.5 |
| Example 6 | 400 | 50 | 74.3 |

EXAMPLES 7–11

In each example, dexamethasone acetate and sodium hyaluronate in amounts shown in Table 2 were dissolved in purified water. The resulting solution was added gradually under stirring at 1,000 rpm into a 1% aqueous acetic acid solution in which purified gelatin had been dissolved in the amount shown in Table 2. After the thus-obtained mixture was stirred for 60 minutes, a solid matter was allowed to occur. The solid matter was collected by filtration, washed with purified water, dried and then ground, whereby a drug composition having the drug content indicated in Table 2 was obtained.

TABLE 2

| | Dexamethasone acetate (mg) | Sodium hyaluronate (mg) | Purified gelatin (mg) | Drug content (%) |
|---|---|---|---|---|
| Example 7 | 50 | 225 | 225 | 15.5 |
| Example 8 | 100 | 200 | 200 | 25.2 |
| Example 9 | 200 | 150 | 150 | 47.9 |
| Example 10 | 300 | 100 | 100 | 60.8 |
| Example 11 | 400 | 50 | 50 | 78.8 |

EXAMPLES 12–16

In each example, dexamethasone acetate and sodium hyaluronate in amounts shown in Table 3 were dissolved in purified water. The resulting solution was added gradually under stirring at 1,000 rpm into a 1% aqueous acetic acid solution in which chitosan had been dissolved in the amount shown in Table 3. After the thus-obtained mixture was stirred for 60 minutes, a solid matter was allowed to occur. The solid matter was collected by filtration, washed with purified water, dried and then ground, whereby a drug composition having the drug content indicated in Table 3 was obtained.

TABLE 3

| | Dexamethasone acetate (mg) | Sodium hyaluronate (mg) | Chitosan (mg) | Drug content (%) |
|---|---|---|---|---|
| Example 12 | 50 | 225 | 225 | 12.2 |
| Example 13 | 100 | 200 | 200 | 26.8 |
| Example 14 | 200 | 150 | 150 | 52.1 |
| Example 15 | 300 | 100 | 100 | 57.1 |
| Example 16 | 400 | 50 | 50 | 55.8 |

EXAMPLES 17–21

In each example, diclofenac sodium and sodium hyaluronate in amounts shown in Table 4 were dissolved in purified water. The resulting solution was added gradually under stirring at 1,000 rpm into a 50% (W/W) aqueous calcium chloride solution (25 g). After the thus-obtained mixture was stirred for 60 minutes, a solid matter was allowed to occur. The solid matter was collected by filtration, washed with ethanol, dried and then ground, whereby a drug composition according to the present invention was obtained with the drug content indicated in Table 4.

TABLE 4

| | Diclofenac sodium (mg) | Sodium hyaluronate (mg) | Drug content (%) |
|---|---|---|---|
| Example 17 | 50 | 225 | 11.9 |
| Example 18 | 100 | 200 | 13.0 |
| Example 19 | 200 | 150 | 21.1 |
| Example 20 | 300 | 100 | 24.9 |
| Example 21 | 400 | 50 | 25.0 |

EXAMPLES 22–26

In each example, diclofenac sodium and sodium hyaluronate in amounts shown in Table 5 were dissolved in purified water. The resulting solution was added gradually under stirring at 1,000 rpm into a 1% aqueous acetic acid solution in which purified gelatin had been dissolved in the amount shown in Table 5. After the thus-obtained mixture was stirred for 60 minutes, a solid matter was allowed to occur. The solid matter was collected by filtration, washed with purified water, dried and then ground, whereby a drug composition having the drug content indicated in Table 5 was obtained.

TABLE 5

|  | Diclofenac sodium (mg) | Sodium hyaluronate (mg) | Purified gelatin (mg) | Drug content (%) |
|---|---|---|---|---|
| Example 22 | 50 | 225 | 225 | 8.8 |
| Example 23 | 100 | 200 | 200 | 19.2 |
| Example 24 | 200 | 150 | 150 | 58.5 |
| Example 25 | 300 | 100 | 100 | 77.3 |
| Example 26 | 400 | 50 | 50 | 79.7 |

EXAMPLES 27–31

In each example, diclofenac sodium and sodium hyaluronate in amounts shown in Table 6 were dissolved in purified water. The resulting solution was added gradually under stirring at 1,000 rpm into a 1% aqueous acetic acid solution in which chitosan had been dissolved in the amount shown in Table 6. After the thus-obtained mixture was stirred for 60 minutes, a solid matter was allowed to occur. The solid matter was collected by filtration, washed with purified water, dried and then ground, whereby a drug composition having the drug content indicated in Table 6 was obtained.

TABLE 6

|  | Diclofenac sodium (mg) | Sodium hyaluronate (mg) | Chitosan (mg) | Drug content (%) |
|---|---|---|---|---|
| Example 27 | 50 | 225 | 225 | 10.3 |
| Example 28 | 100 | 200 | 200 | 16.3 |
| Example 29 | 200 | 150 | 150 | 32.5 |
| Example 30 | 300 | 100 | 100 | 49.6 |
| Example 31 | 400 | 50 | 50 | 75.7 |

Test 1

With respect to the drug compositions prepared in EXAMPLES 2, 4, 7, 9, 12 and 14, a release test was conducted using water (37° C.) as a release test fluid. As a control, bulk powder of dexamethasone acetate was used. The results are shown in FIG. 1. It has been confirmed from FIG. 1 that the release of a drug from a drug composition can be controlled as desired by changing the kind of at least one of materials employed for the formation of a matrix.

EXAMPLE 32

Sodium hyaluronate (viscosity average molecular weight: approximately 1,000,000, 1,000 mg) was dissolved in purified water (100 ml). The resulting solution was added gradually under stirring at 1,000 rpm into a 50% (W/W) calcium chloride solution (500 g). After the thus-obtained mixture was stirred for 60 minutes, a solid matter was allowed to occur. The solid matter was collected by filtration, washed with ethanol, dried and then ground, whereby a drug composition was obtained.

EXAMPLE 33

Sodium hyaluronate (viscosity average molecular weight: approximately 1,000,000, 1,000 mg) was dissolved in purified water (100 ml). The resulting solution was added gradually under stirring at 1,000 rpm into a solution of purified gelatin (1,000 mg) in a 1% aqueous acetic acid solution (99 g). After the thus-obtained mixture was stirred for 60 minutes, a solid matter was allowed to occur. The solid matter was collected by filtration, washed with purified water, dried and then ground, whereby a drug composition was obtained.

EXAMPLE 34

Sodium hyaluronate (viscosity average molecular weight: approximately 1,000,000, 1,000 mg) was dissolved in purified water (100 ml). The resulting solution was added gradually under stirring at 1,000 rpm into a solution of albumin (1,000 mg) in a 1% aqueous acetic acid solution (99 g). After the thus-obtained mixture was stirred for 60 minutes, a solid matter was allowed to occur. The solid matter was collected by filtration, washed with purified water, dried and then ground, whereby a drug composition was obtained.

EXAMPLE 35

Sodium hyaluronate (viscosity average molecular weight: approximately 1,000,000, 1,000 mg) was dissolved in purified water (100 ml). The resulting solution was added gradually under stirring at 1,000 rpm into a solution of ferric chloride (1,000 mg) in purified water (99 g). After the thus-obtained mixture was stirred for 60 minutes, a solid matter was allowed to occur. The solid matter was collected by filtration, washed with purified water, dried and then ground, whereby a drug composition was obtained.

EXAMPLE 36

Sodium hyaluronate (viscosity average molecular weight: approximately 1,000,000, 1,000 mg) was dissolved in purified water (100 ml). The resulting solution was added gradually under stirring at 1,000 rpm into a solution of poly-L-lysine (1,000 mg) in a 1% aqueous acetic acid solution (99 g). After the thus-obtained mixture was stirred for 60 minutes, a solid matter was allowed to occur. The solid matter was collected by filtration, washed with purified water, dried and then ground, whereby a drug composition was obtained.

EXAMPLE 37

Sodium hyaluronate (viscosity average molecular weight: approximately 1,000,000, 1,000 mg) was dissolved in purified water (100 ml). The resulting solution was added gradually under stirring at 1,000 rpm into a solution of chitosan (1,000 mg) in a 1% aqueous acetic acid solution (99 g). After the thus-obtained mixture was stirred for 60 minutes, a solid matter was allowed to occur. The solid matter was collected by filtration, washed with purified water, dried and then ground, whereby a drug composition was obtained.

EXAMPLE 38

Sodium hyaluronate (viscosity average molecular weight: approximately 1,000,000, 1,000 mg) was dissolved in purified water (100 ml). The resulting solution was added gradually under stirring at 1,000 rpm into a solution of sodium casein (100 mg) in a 1% aqueous acetic acid solution (99.9 g). After the thus-obtained mixture was stirred for 60 minutes, a solid matter was allowed to occur. The solid matter was collected by filtration, washed with purified water, dried and then ground, whereby a drug composition was obtained.

Test 2

Figure 2:
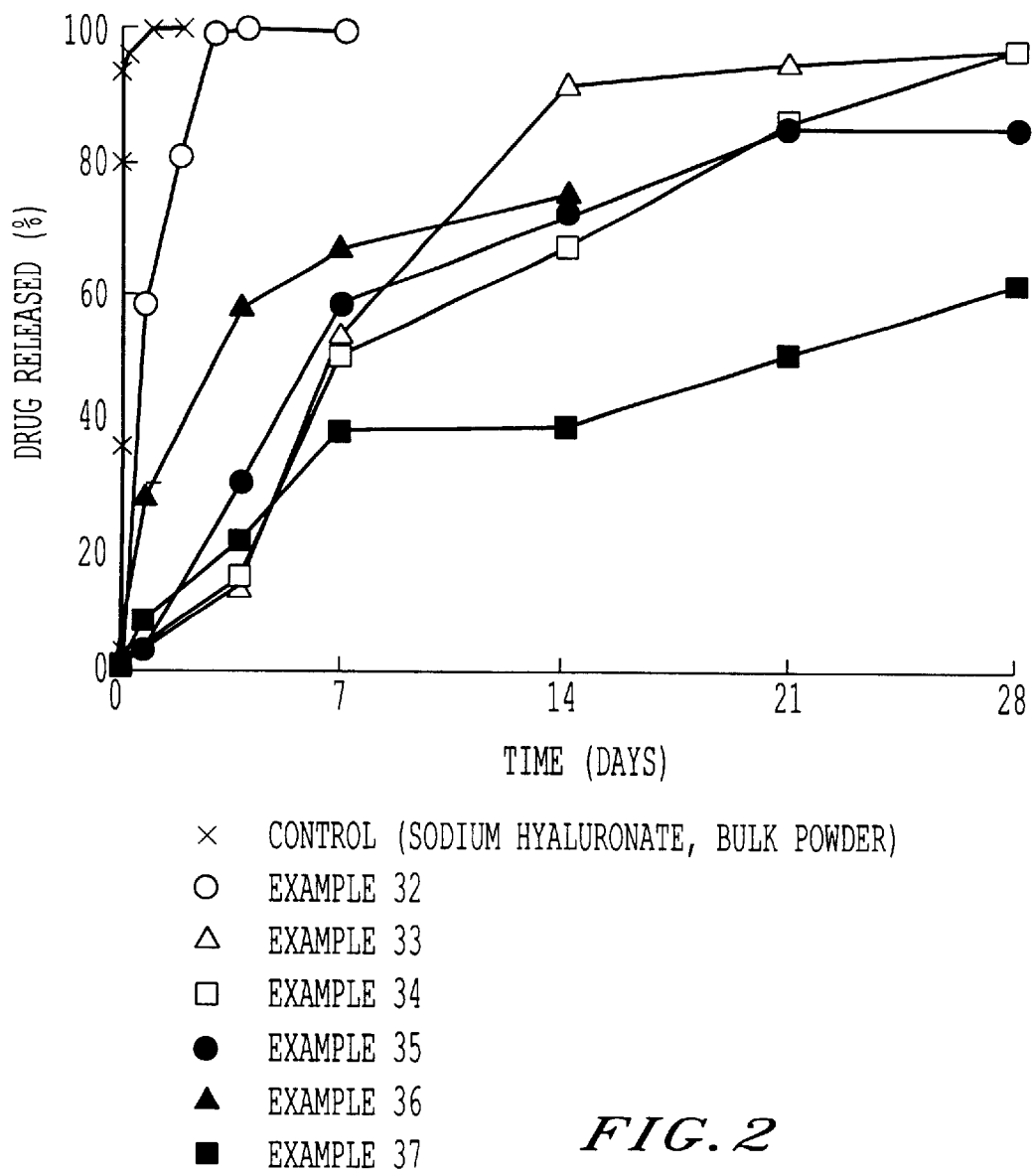
FIG. 2 is a graph depicting release profiles of hyaluronic acid from drug compositions, which had been prepared using substances of different kinds, into water.

With respect to the drug compositions prepared in Examples 32–37, a release test was conducted using water (37° C.) as a release test fluid. Namely, the test was conducted by adding the drug compositions in amounts equivalent to 2 mg of hyaluronic acid in 3-ml aliquots of purified water, respectively. As a control, bulk powder of sodium hyaluronate was used. The results are shown in FIG. 2. It has been confirmed from FIG. 2 that the release of hyaluronic acid from a drug composition can be controlled as desired by changing the kind of at least one of materials employed for the formation of a matrix.

EXAMPLE 39

Sodium hyaluronate (viscosity average molecular weight: approximately 1,000,000, 1,000 mg) was dissolved in purified water (100 ml). The resulting solution was added to medium-chain fatty acid triglyceride (200 g), and the thus-obtained mixture was stirred at 2,500 rpm into an emulsion by a marine propeller stirrer. The emulsion, while being maintained under stirring at 1,200 rpm by the marine propeller stirrer, was added to a 50% (W/W) aqueous calcium chloride solution (600 ml). After the thus-obtained mixture was stirred for 60 minutes, microspheres were allowed to occur. The microspheres were collected by filtration, washed with ethanol and then dried. The microspheres so obtained had an average particle size of 78.4 $\mu$m and a hyaluronic acid content of 78.1%.

EXAMPLE 40

Sodium hyaluronate (viscosity average molecular weight: approximately 1,000,000, 1,000 mg) was dissolved in purified water (100 ml). The resulting solution was added to medium-chain fatty acid triglyceride (200 g), and the thus-obtained mixture was stirred at 2,500 rpm into an emulsion by a marine propeller stirrer. The emulsion, while being maintained under stirring at 1,200 rpm by the marine propeller stirrer, was added to a 1% aqueous acetic acid solution (594 g) in which chitosan (6,000 mg) had been dissolved. After the thus-obtained mixture was stirred for 60 minutes, microspheres were allowed to occur. The microspheres were collected by filtration, washed with ethanol and then dried. The microspheres so obtained had an average particle size of 63.4 $\mu$m and a hyaluronic acid content of 86.2%.

EXAMPLE 41

Sodium hyaluronate (viscosity average molecular weight: approximately 600,000, 500 mg) was dissolved in purified water (100 ml). The resulting solution was added to medium-chain fatty acid triglyceride (200 g), and the thus-obtained mixture was stirred at 3,000 rpm into an emulsion by a marine propeller stirrer. The emulsion, while being maintained under stirring at 1,200 rpm by the marine propeller stirrer, was added to a 1% aqueous acetic acid solution (594 g) in which chitosan (6,000 mg) had been dissolved. After the thus-obtained mixture was stirred for 60 minutes, microspheres were allowed to occur. The microspheres were collected by filtration, washed with ethanol and then dried. The microspheres so obtained had an average particle size of 31.2 $\mu$m.

EXAMPLE 42

Sodium hyaluronate (viscosity average molecular weight: approximately 2,000,000, 2,000 mg) was dissolved in purified water (100 ml). The resulting solution was added to medium-chain fatty acid triglyceride (200 g), and the thus-obtained mixture was stirred at 2,000 rpm into an emulsion by a marine propeller stirrer. The emulsion, while being maintained under stirring at 1,200 rpm by the marine propeller stirrer, was added to a 1% aqueous acetic acid solution (594 g) in which chitosan (6,000 mg) had been dissolved. After the thus-obtained mixture was stirred for 60 minutes, microspheres were allowed to occur. The microspheres were collected by filtration, washed with ethanol and then dried. The microspheres so obtained had an average particle size of 142.3 $\mu$m.

EXAMPLE 43

Sodium hyaluronate (viscosity average molecular weight: approximately 600,000, 500 mg) was dissolved in purified water (100 ml). Using a needle-tipped syringe, the resulting solution was added dropwise little by little into a solution of chitosan (6,000 mg) in a 1% aqueous acetic acid solution (594 g). After the thus-obtained mixture was gently stirred for 60 minutes, microspheres were allowed to occur. The microspheres were collected by filtration, washed with ethanol and then dried. The microspheres so obtained had an average particle size of 495.5 $\mu$m.

Test 3

Figure 3:
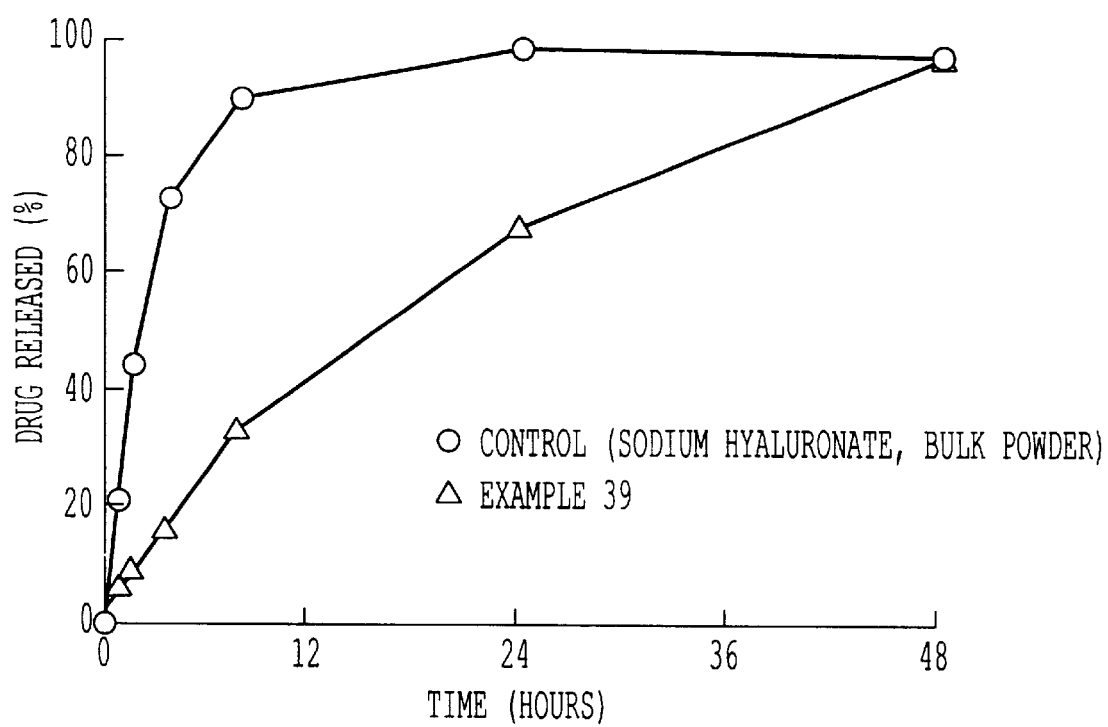
FIG. 3 is a graph illustrating release profiles of hyaluronic acid from microspheres which had been prepared using calcium chloride and contained sodium hyaluronate.

With respect to the microspheres prepared in Example 39, a release test was conducted using water (37° C.) as a release test fluid. Namely, the test was conducted by adding the microspheres in an amount equivalent to 2 mg of hyaluronic acid in purified water (3 ml). As a control, bulk powder of sodium hyaluronate was used. The results are shown in FIG. 3. It has been confirmed from FIG. 3 that the release of hyaluronic acid from the microspheres was delayed compared with that hyaluronic acid from bulk powder of sodium hyaluronate.

EXAMPLES 44–45

To distinguish from sodium hyaluronate existing in the living body, two types of microspheres were obtained in a similar manner as in Example 39 by using two sodium hyaluronate samples labeled with a fluorescent substance (fluorescamine), respectively. The viscosity average molecular weights of these two sodium hyaluronate samples were approximately 1,000,000 and approximately 2,000,000 respectively. The microspheres, which had been obtained using the sodium hyaluronate sample having the molecular weight of approximately 1,000,000, had an average-particle size of 68.7 $\mu$m and a fluorescence-labeled hyaluronic acid content of 89.0% (Example 44), while the microspheres, which had been obtained using the sodium hyaluronate sample having the molecular weight of approximately 2,000,000, had an average particle size of 64.3 $\mu$m and a fluorescence-labeled hyaluronic acid content of 82.4%. (Example 45).

Test 4

Figure 4:
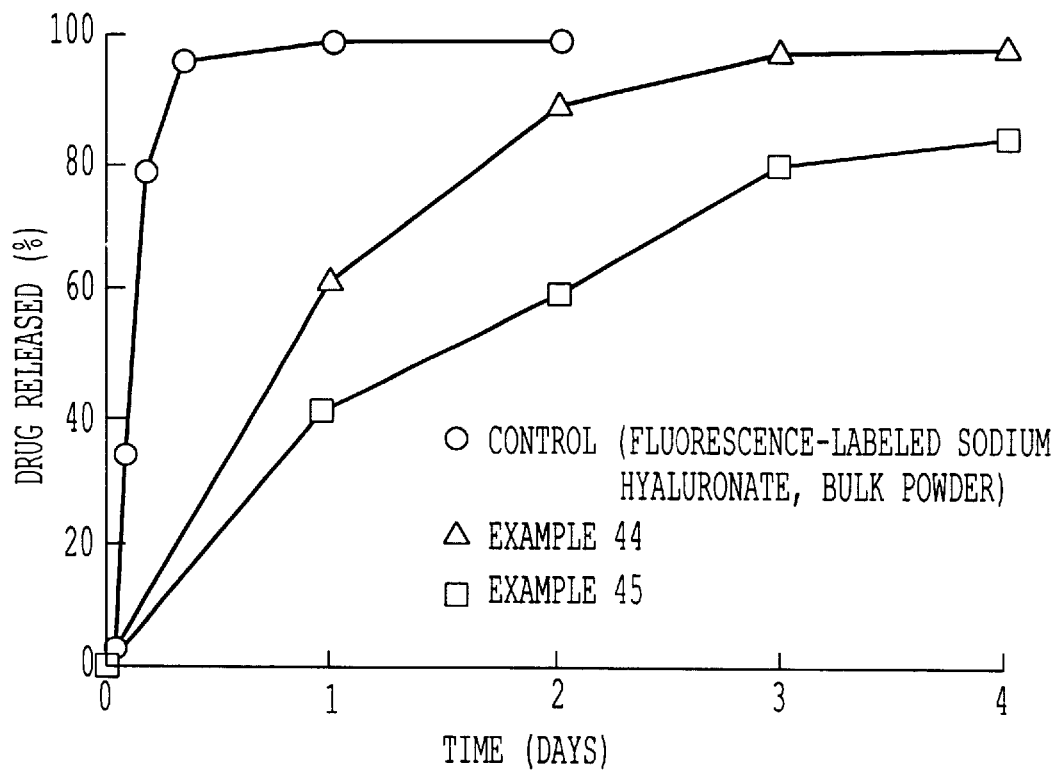
FIG. 4 is a graph showing release profiles of fluorescence-labeled hyaluronic acid from microspheres which had been prepared using calcium chloride and contained sodium fluorescence-labeled hyaluronate.

With respect to the microspheres prepared in Examples 44 and 45, a release test was conducted in a similar manner as in Test 1. The results are shown in FIG. 4. As is evident from FIG. 4, the microspheres obtained from the sodium hyaluronate sample having the molecular weight of approximately 2,000,000 (Example 45) exhibited slower release than those obtained from the sodium hyaluronate sample having the molecular weight of approximately 1,000,000 (Example 46), and the microspheres obtained from the sodium hyaluronate sample having the molecular weight of approximately 1,000,000 showed substantially the same release as the sample of Example 39 prepared by using hyaluronic acid not labeled with fluorescence (see FIG. 3).

Test 5

Figure 5:
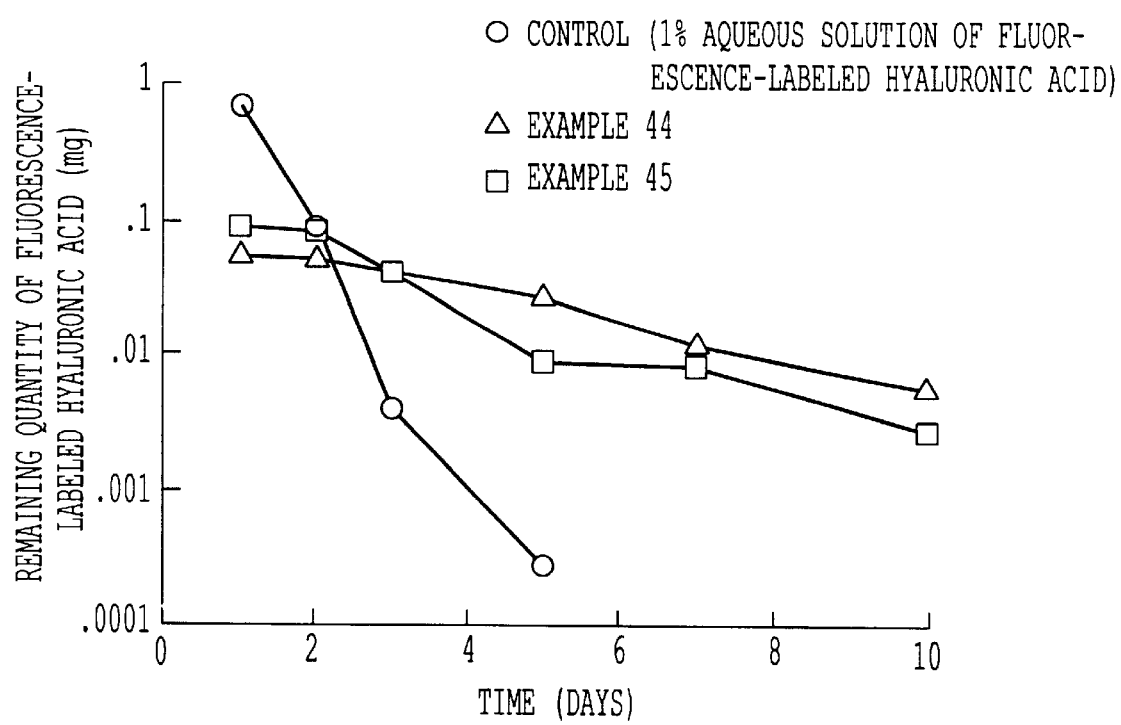
FIG. 5 is a graph depicting quantities of fluorescence-labeled hyaluronic acid remaining in knee joints of rabbits when an aqueous solution of fluorescence-labeled hyaluronic acid and microspheres containing fluorescence-labeled sodium hyaluronate were administered to the knee joints, respectively.

The microsphere samples (6 mg), which had been prepared in Examples 44 and 45, were suspended in aliquots of an injection-grade dispersion medium which was composed of injection-grade water, an isotonicity, a suspending agent, etc., and were then administered into knee joints of rabbits, respectively. The fluorescence-labeled hyaluronic acid remaining in each knee joint was periodically quantitated to determine the in vivo residence property of the drug. As a control, a 1% aqueous solution (3 mg) of fluorescence-labeled hyaluronic acid was administered. The results are shown in FIG. 5. Compared with the aqueous solution of fluorescence-labeled hyaluronic acid, the administration of the microspheres with fluorescence-labeled hyaluronic acid contained therein resulted in the maintenance of fluorescence-labeled hyaluronic acid over a longer time within the knee joint. Microspheres with hyaluronic acid contained therein have therefore been confirmed to permit control of the release of hyaluronic acid and hence control of its in vivo duration time.

EXAMPLE 46

Sodium hyaluronate (viscosity average molecular weight: approximately 1,000,000, 900 mg) was dissolved in purified water (90 ml). Dexamethasone acetate (106 mg) was then added, followed by thorough dispersion. The resulting dispersion was added to medium-chain fatty acid triglyceride (200 g), and the thus-obtained mixture was stirred at 2,500 rpm into an emulsion by a marine propeller stirrer. The emulsion, while being maintained under stirring at 1,200 rpm by the marine propeller stirrer, was added to a 50% (W/W) aqueous calcium chloride solution (600 ml). After the thus-obtained mixture was stirred for 60 minutes, microspheres were allowed to occur. The microspheres were collected by filtration, washed with ethanol and then dried.

EXAMPLE 47

Sodium hyaluronate (viscosity average molecular weight: approximately 1,000,000, 900 mg) was dissolved in purified water (90 ml). Dexamethasone acetate (100 mg) was then added, followed by thorough dispersion. The resulting dispersion was added to medium-chain fatty acid triglyceride (200 g), and the thus-obtained mixture was stirred at 2,500 rpm into an emulsion by a marine propeller stirrer. The emulsion, while being maintained under stirring at 1,200 rpm by the marine propeller stirrer, was added to a solution of chitosan (6,000 mg) in a 1% aqueous acetic acid solution (594 g). After the thus-obtained mixture was stirred for 60 minutes, microspheres were allowed to occur. The microspheres were collected by filtration, washed with ethanol and then dried.

Capability of Exploitation in Industry

The drug composition according to the present invention, which makes use of a high-molecular substance or the like and hyaluronic acid or the like as a drug carrier, has biodegradability and biocompatibility, and can control the release of its drug. When administered in vivo, the pharmacological effects can be exhibited for a desired time.

What is claimed is:

1. A drug composition with a controlled drug release rate, comprising:
   a matrix formed of the following ingredients (a) and (b):
     (a) a biodegradable, biocompatible high-molecular substance and/or polyvalent metal ions or polyvalent metal ion source, and
     (b) hyaluronic acid or a salt thereof; and
   a drug incorporated as an ingredient (c) in said matrix, wherein said ingredient (b) has a viscosity average molecular weight of from 600,000 to 2,000,000.

2. The drug composition according to claim 1, wherein said ingredient (a) is at least one high-molecular substance or polyvalent metal ions selected from the group consisting of polypeptides, polyamino acids, cationic polysaccharides, and polyvalent metal ions.

3. The drug composition according to claim 1 or 2, wherein said ingredient (a) is at least one high-molecular substance or polyvalent metal ions selected from the group consisting of gelatin, sodium casein, albumin, lysozyme chloride, poly-L-lysine, chitosan, $Ca^{2+}$, $Al^{3+}$, and $Fe^{3+}$.

4. The drug composition according to claim 1 or 2, wherein said ingredient (c) is at least one drug selected from the group consisting of anti-inflammatory drugs, antiepileptics, hypnotic sedatives, antipyretic analgesics, stimulants, antihypnotics, drugs for vertigo, drugs for the central nervous system, skeletal muscle relaxants, drugs for the autonomic nervous system, autonomic ganglionic blockers, drugs for the peripheral nervous system, opthalmic drugs, drugs for sense-organs, cardiacs, antiarrhythmics, diuretics, antihypertensives, vasoreinforcements, vasoconstrictors, vasodilators, antiarteriosclerotics, circulatory drugs, respiratory stimulants, antitussive expectorants, drugs for respiratory organs, peptic ulcer drugs, stomachic digestants, antacids, cathartics, cholagogues, digestive drugs, hormonal agents, urinary tract disinfectants, uterotonics, urogenital drugs, drugs for anus diseases, vitamins, nutritive roborants, drugs for blood or body fluid, drugs for hepatic diseases, antidotes, habitual intoxication drugs, antipodagrics, enzyme preparations, antidiabetics, cell activation drugs, antitumor agents, antibiotics, chemotherapeutic agents, and arthritis therapeutics.

5. The drug composition according to claim 1 or 2, wherein the content of said ingredient (c) is not higher than 90 wt. %.

6. The drug composition according to claim 1 or 2, which is in the unit dosage form of micro-capsules.

7. The drug composition according to claim 6, wherein said microcapsules have an average particle size of from 30 to 500 μm.

8. The drug composition according to claim 1 or 2, which is in a unit dosage form of an injection, oral preparation, external preparation, suppository or implant.

9. The drug composition according to claim 1 or 2, which has been prepared by submerged hardening or submerged dropping hardening.

10. A drug composition according to claim 1, wherein said ingredient (a) is a cationic polysaccharide.

11. A drug composition according to claim 10, wherein said cationic polysaccharide comprises chitosan.

12. The drug composition according to claim 1, wherein ingredient (a) is $Ca^{+2}$.

13. The drug composition according to claim 1, wherein ingredient (a) is gelatin.

* * * * *